United States Patent [19]

Colon et al.

[11] Patent Number: 4,681,576
[45] Date of Patent: Jul. 21, 1987

[54] WETNESS INDICATING HOT-METAL ADHESIVES

[75] Inventors: Herman Colon, Monsey, N.Y.; Albert Maletsky, Franklin Lakes, N.J.

[73] Assignee: Malcolm Nicol & Co., Lyndhurst, N.J.

[21] Appl. No.: 839,943

[22] Filed: Mar. 17, 1986

[51] Int. Cl.$^4$ .................. A61F 13/16; A61F 13/18; A61F 13/20; C08J 23/00

[52] U.S. Cl. .................. 604/361; 524/271; 524/272; 524/275; 524/322; 524/718

[58] Field of Search ............ 524/271, 272, 275, 322, 524/718; 128/284; 604/287, 290 R, 361

[56] References Cited

U.S. PATENT DOCUMENTS

| | | | |
|---|---|---|---|
| 3,731,685 | 5/1973 | Eidus | 128/284 |
| 3,952,746 | 4/1976 | Summers | 128/287 |
| 4,231,370 | 11/1980 | Mroz et al. | 128/287 |
| 4,325,851 | 4/1982 | Colon et al. | 524/83 |
| 4,331,576 | 5/1982 | Colon et al. | 524/271 |

Primary Examiner—Morton Foelak
Assistant Examiner—Dennis R. Daley
Attorney, Agent, or Firm—Erwin S. Teltscher

[57] ABSTRACT

A wetness indicating hot-melt adhesive which changes color quickly in response to the presence of moisture is disclosed which contains 20 to 70 wt. % of polymer, 35 to 100 wt. % of which is water sensitive polymer; 27 to 60 wt. % of organic acid which is selected from a high acid number fatty acid or a combination of a high acid number fatty acid and other high acid number organic acids; 0 to 30 wt. % of water soluble wax and a wetness indicating agent which changes the color of the composition rapidly in response to moisture therein.

14 Claims, No Drawings

WETNESS INDICATING HOT-METAL ADHESIVES

FIELD OF THE INVENTION

This invention relates to wetness indicators. More specifically this invention concerns wetness indicating hot-melt adhesion compositions.

BACKGROUND OF THE INVENTION

Hot melt adhesives are well known. Generally, hot-melt adhesives are applied by melting the adhesive composition and applying a coat of the molten adhesive layer on a substrate. The coated material is then cooled to harden the adhesive layer and is ready for storage. Among the hot-melt adhesives that have been found useful and economically important are remoistenable hot-melt adhesives and remoistenable pressure-sensitive hot-melt adhesives.

Water activatable adhesives applied from water-based media are commonly used as envelope-flap adhesives, postage-stamp adhesives, binding tapes, sealing tapes, diapers and the like. Now, remoistenable hot-melt adhesives can be used for similar applications. For such use, it is desirable that the hot-melt coating be capable of storage without blocking, i.e. adhering due to activating of the adhesive of combination of ambient humidity, temperature and contact pressure. In addition, the dried adhesive, when contacted with water, must be uniformly activated and capable of developing an adherent bond between the coated surface and an uncoated surface. The hot-melt characteristics of the formulations are also important. The adhesive should have good pot life, at least 30–40 hours at usual application temperatures of about 350° F., as well as low viscosity characteristics at these temperatures, and the viscosity of the hot-melt should be substantially constant during the pot-life of the hot-melt.

As a result of previous work in this field, a water activatable adhesive which has excellent non-blocking and water activatable adhesive characteristics, and also excellent hot-melt characteristics has been found, as disclosed in U.S. Pat. No. 4,325,851.

Pressure sensitive hot-melt adhesives are useful for the adhesive coating of labels, cloth patches and the like. A water soluble pressure-sensitive hot-melt adhesive composition with excellent adhesive properties has been disclosed in U.S. Pat. No. 4,331,576. Labels comprised of this water soluble pressure-sensitive hot-melt adhesive composition adhere permanently to substrates under normal conditions; on the other hand, when wet, such labels can be removed readily without damage to the substrate.

Non-pressure sensitive hot-melt adhesives have been used as the adhesive medium for multiline construction of disposable baby and adult diapers, sanitary napkins and hospital bed pads. In this construction the adhesive is applied in longitudinal, parallel or bead multi-lines to laminate a polyolefin film which forms the outer shell to tissues or non-woven substrates. It is often desirable to know if it is wet and thus a hot melt adhesive used in this capacity, and yet signaling the presence of water by a color change is invaluable.

An example of a non-pressure sensitive water based latex adhesive which when dry, signals the presence of water by a color change is taught in U.S. Pat. No. 4,231,370, issued to Mroz et al. According to this disclosure a flexible pH-change/color wetness indicator is coated on a surface portion of the product, which is visible through the cover member, and which retains sharp edge definition of the coated surface portion when wetted, for example, by urine. Such a coating includes a pH-change/color-change type material dispersed in a polymer latex matrix composed of styrene/2-ethylhexyl-acrylate copolymer, vinyl acetate-/ethylene copolymer and polyvinyl acetate. To obtain a suitable pH, sufficient acid buffering means, such as phosphoric acid must be used; this is a harsh acid which could conceivably hurt a child.

It is a disadvantage of the broadly similar prior art Mroz et al composition, that the adhesive material can only be obtained by evaporation from a water-based latex composition. This means that equipment must be provided during the manufacture of the Mroz et al product which can release the water present. Also such problems as foaming, and proper wetting of the substrate must overcome, all resulting in a more expensive manufacturing process of the Mroz et al formula. It is another disadvantage that any color change of the Mroz et al composition takes a very long time to take effect, e.g. of the order of 3 minutes, as can be seen, for example, from FIGS. 3 and 4 of the Mroz et al patent.

Further, the time required for the color change in the Mroz et al composition is dependent on the thickness of the coating, as well as the pH of the wetting composition; the thicker the coating and the lower the pH, the slower the color change.

It is often desirable to know quickly, by visual inspection, whether a substrate has become wet. For example, it is desirable to know when a diaper has become wet, but the wetness of a diaper which is plastic coated, or which is worn under a water proof panty, is not readily determined by visual inspection.

SUMMARY OF THE INVENTION

An object of the present invention is the provision of a hot-melt adhesive composition which is capable of indicating the presence of water therein.

Another object of the present invention is the provision of a hot-melt adhesive composition which changes color in response to wetness.

A further object of the present invention is the provision of a hot-melt adhesive which changes color rapidly when wet. Another object of the present invention is the provision of a hot melt adhesive coating which changes color rapidly when wet, independent of the thickness of the coating and substantially independent of the pH of the wetting composition.

A particular object of the present invention is the provision of a hot-melt adhesive composition which is effective to show quickly that a diaper has become wet.

These and other objects are accomplished by the present invention.

A wetness indicating composition has been discovered which adheres substantially to any substrate, and which provides immediate recognition, by visual inspection, that the substrate has become wet.

According to the invention, the wetness indicating composition is composed of a hot-melt adhesive composition and a wetness indicating agent which causes the composition to change color in response to the presence of water in the composition.

The wetness indicating hot-melt adhesive composition of the invention comprises:

(A) 20 to 70 wt.% of total polymer components, said polymer components comprising 35 to 100 wt.% of water sensitive polymer selected from vinyl pyrrolidone homopolymer, vinyl pyrrolidone/vinyl acetate copolymer or a mixture thereof, any balance comprising at least one polymer selected from the group consisting of ethylene vinyl acetate copolymer, ethylene/acrylic acid copolymer and polyamide;

(B) 27 to 60 wt.% of an acidic composition selected from
  (a) at least one free monobasic saturated or unsaturated fatty acid having an acid number above 137 or
  (b) 15 to 50 wt.% of the fatty acid in combination with 10 to 55 wt.% of at least one other organic acid having an acid number above 130;

(C) 0 to 30 wt.% of a water soluble wax; and (D) a wetness indicating agent capable of causing the composition to change color in response to the presence of moisture in the composition, in an amount effective to provide the composition with a readily visible color when wet, which is distinct from the color of the dry composition.

In a particular embodiment of the invention, a device, such as a label, tape, or plastic, which can be coated with a hot-melt, is coated with the wetness indicating hot-melt adhesive composition of the invention.

Another embodiment of the invention is a diaper which contains the wetness indicating hot-melt adhesive composition of the invention.

DETAILED DESCRIPTION AND PREFERRED EMBODIMENTS OF THE INVENTION

The polymer component of the wetness indicating hot-melt adhesive composition of the invention is based on water sensitive resin which is selected from vinyl pyrrolidone homopolymer (VP) and vinyl pyrrolidone/vinyl acetate copolymer (VP/VA) and mixtures thereof. In the copolymer, the proportion of the monomer components ranges from 3:1 to 1:3 by weight of each monomer moiety. Within this range the flow points of the copolymer are satisfactory for the hot-melt formulations of this invention.

A satisfactory copolymer in the solid state is marketed by GAF Corp. (NYC, N.Y., USA) under the trade name PVP/VA S630. This is a 60/40 VP/VA copolymer. Other polymers of different proportions are commercially available with most being marketed in solution form by GAF (USA) and BASF (W. Germany). A useful vinyl pyrrolidone homopolymer is marketed by BASF, under the tradename Luviskol. Products in solution form require removal of the solvents before or during the preparation of the hot-melt. The water sensitivity of these copolymers provides the water activatable or water sensitive property of the final adhesive formulation, when coated on the substrate.

Optionally, one or more additional polymers compatible with VP or VP/VA may be included in the adhesive composition of the invention. For example, ethylene/vinyl acetate copolymer (E/VA), ethylene/acrylic acid copolymer (E/AA) and polyamides (PA) are compatible with VP and VP/VA, and useful in the present formulations.

Such ethylene/vinyl acetate copolymers are marketed by several companies such as duPont (Delaware USA) under the "Elvax" trade name. The vinyl acetate content of these copolymers suitable for inclusion in the formulations of this invention ranges from about 17 to 29%. Preferred are the copolymers at the lower end of the range, as they are the most compatible with the VP/VA copolymers. The Elvax 410 series copolymer having a VA content of 17.5 to 18.5% is most preferred; it has a melt index (ASTM D 1238) of 455–550. The E/VA copolymer, unlike the VP/VA copolymer, is not water sensitive. It has been used as a major polymer component in direct sealing hot-melt adhesives, that is, in adhesives where the melt is applied and the surfaces joined before the melt solidifies.

Ethylene/acrylic acid copolymers suitable for use in the present compositions are produced by Allied Chemical Co. under the Allied Chemical trade name. Allied Chemical Co. does not provide the copolymer ratios, but indicates the acid number to be between 40 and 75 for these specialty products.

The polyamide can be either of low amine number type (10–28) or of high acid number (80–140). The lower amine polyamide is produced by Emery Inc., while the high acid number polyamide is produced by Crosby Inc. of Los Angeles.

The total polymer content of the compositions of the invention may range from 20 to 70 wt.%, of which 35 to 100 wt.% is VP or VP/VA, and any remainder is selected from another polymer or copolymer such as E/VA, E/AA, PA and a combination thereof. More preferably, the compositions of the invention contain about 30 to 65 wt.% of total polymer. It is also more preferable that at least 50 wt.% of the polymer components be VP/VA, VP, or a combination thereof.

Fatty acids useful for the present invention are liquid aliphatic straight chain free fatty acids. Other high acid number (more than 130) organic acids such as high acid number rosin, hydrogenated rosin or tall oil may be used in conjunction therewith.

Commercial liquid fatty acids may be blended with each other or with other high acid number organic acids including rosin and tall oil products. The acids, when mixed, should be able to withstand 350° F. for 48 hrs., without any serious chemical degradation as evidenced by color or odor.

High acid number fatty acids, which contain at least 14 carbon atoms, when used alone, i.e. without other types of organic acids, may be present in an amount of 27 to 60 wt.%, depending on the desired characteristic of the adhesive. Alternately, when used in combination with other high acid number organic acids, the fatty acids may be present in an amount of 15 to 50 wt.%, while the other organic acids make up the remaining acid requirements, i.e. 10 to 55 wt.%.

When a pressure sensitive hot-melt adhesive is desired, it is preferable that the fatty acid should be used in an amount of 27 to 60 wt.%, more preferably 35 to 50 wt.% of the composition. It is also preferable that the proportion of fatty acid to total polymer in the composition be from 1:2 to 2:1. For example at a weight range of 13 or 14 wt.% of fatty acid alone, the desired results are not achieved; a composition with this proportion of acid components is suitable as a remoistenable hot-melt adhesive only, but will not produce any change in color.

If desired, waxy materials selected from solid water soluble, waxy, polyethylene glycols or polyoxyethylene glycols (PEG) may be included in the wetness indicating adhesive composition of the invention in an amount up to 30 wt.% of the invention to modify the physical properties of the composition. Commercial water soluble solid PEG waxes range in molecular weight from about 4,000 to about 20,000 and are marketed by Union Carbide under the Carbowax trade name; equivalent materials are available from other sources.

As the wetness indicating agent, a material which is compatible with the instant compositions, or VP and VP/VA polymers in particular, and which is capable of changing the color of the adhesive composition quickly when the adhesive composition is wet, compared to the color of the dry adhesive composition, may be used in the present wetness indicating adhesive composition. Acid-base indicators, which change color in response to a change in pH, are preferred, because they change color rapidly, and those providing a change to a bright, vivid color are generally most preferred. Other materials which change color in response to water may be used as the wetness indicating agent, such as dyes which are substantially invisible in the dry composition, which quickly become a vivid color when wet. An example of such a material is the blue dye Calcocid Blue 2G made by American Cyanamide Corp.

Acid-base indicators for use in the present compositions are those which change color at a pH in the range of about 3 to 7, such as Ethyl Red, Bromophenol Blue (made by Eastman Kodak), or Bromocresol Green mixed with Bromophenol Blue; Bromophenol Blue is particularly preferred. The wetness indicating agent is used in an amount effective to provide the composition with a readily visible color when the composition is wet, and of course, the readily visible color must be easily distinguishable from the color of the dry composition; generally about 0.05 to 0.1 wt.% pf indicator, based on the weight of the composition, is adequate.

Optional components of the compositions of the invention include antioxidants, which may be added in an amount of about 0.05 to 0.1 wt.%, rosins, such as Sylvatac 95, (made by Sylvachem Corp.), plasticizer, such as Dantocol, surfactants, essential oils and perfumes and similar special purpose additives common in this art, and are within the ambit of the invention.

Compared to compositions of the prior art, color change in the composition, according to the present invention, is very fast, and substantially independent of the thickness of the composition of the coating applied to a substrate and of pH range within certain limits of the wetting composition. Thus a change in color is obtained within 5-30 seconds. This can be faster, depending of the shape of the beadline.

The following examples of the invention are for the purpose of illustrating representative compositions preferred for specific uses, and it must be realized that no single formulation is satisfactory for all substrates. All proportions are by weight unless otherwise indicated.

EXAMPLE 1

The antioxidant, Irganox 1010 (manufactured by Ciba-Geigy) in an amount of 0.1 wt.% and about 0.05 wt.% Bromophenol Blue were mixed with the other nonpolymer components until uniform, with heating and then the polymer was added with continued heating at a temperature of about 160°-177° C. with stirring until dissolved.

The proportion of fatty acid and polymer components was as follows:

| | |
|---|---|
| Fatty acid (Emersol 871) | 36 wt. % |
| Ethylene/acrylic acid copolymer (AC-580) | 18 wt. % |
| Vinyl pyrrolidone/vinyl acetate copolymer | 100 wt. % |
| (Gantron PVP) to make up | |

This adhesive product can be applied to a substrate, such as a polyethylene film, in an amount sufficient to cause the polyethylene film to adhere to another substrate, such as absorbent, non-woven material. When the absorbent material is wet, the adhesive product immediately turns bright blue.

EXAMPLES 2-6

These examples have been prepared as described in Example 1, and contain 0.1 wt.% of the antioxidant, Irganox 1010, 0.07 wt.% of the pH indicator Bromophenol Blue, as well as polymer, water soluble wax, and fatty acid in the amounts shown in Table 1.

In these examples the following material have been used.

Polymer: Gantron S630; vinyl pyrrolidone/vinyl acetate copolymer
Fatty acid: Emersol 871 in Examples 2–4 and 6 Emersol 150 in Example 5
Water soluble wax: Carbowax 4000

TABLE 1

| | EXAMPLE | | | | |
|---|---|---|---|---|---|
| Component | 2 | 3 | 4 | 5 | 6 |
| Polymer | 40 | 40 | 54.6 | 54.6 | 20.0 |
| Fatty acid | 50 | 40 | 27.3 | 27.3 | 53.3 |
| Water sol. wax | 10 | 20 | 18.1 | 18.1 | 26.7 |

The hot-melt of examples 2-5 forms an adhesive film on a substrate such as paper, polyethylene or polypropylene, which is light yellow in color. When wet, the film turns bright blue immediately. Example 6 is a light yellow gel, which changes to a bright blue color in response to wetness.

EXAMPLE 7

In combination with 0.1 wt.% of the antioxidant, Irganox 1010 and 0.07 wt.% of Bromophenol Blue, the following components were mixed under the conditions described in Example 1.

| | |
|---|---|
| Pyrrolidone homopolymer (Luviskol K-30) | 30.00 wt. % |
| Ethylene/vinyl acetate copolymer (Elvax 410) | 20.00 wt. % |
| High acid no cpd., i.e. fatty acid (Emersol 871) to make up | 100.00 wt. % |

This product forms an adherent film, light yellow in color, on a substrate such as paper, polyethylene, or polypropylene, which turns bright blue immediately when wet with water.

EXAMPLES 8-10

The formulation in Table 2, plus 0.1 wt.% of the antioxidant Irganox 1010 and 0.07 wt.% of the pH indicator, Bromophenol blue, yield products which form light yellow colored, adherent films on substrates such as paper, polyethylene, polyester non-woven fibers, and polypropylene. The films are effective to cause the substrate to adhere to another material, and become bright blue in color in response to contact with a wet paper towel.

TABLE 2

| Component | EXAMPLE | | |
|---|---|---|---|
| | 8 | 9 | 10 |
| Vinyl pyrrolidone/vinyl acetate copolymer (Gantron) | 40 | 36.3 | 45.5 |
| Ethylene/vinyl acetate copolymer (Elvax 410) | 10 | 18.2 | 18.2 |
| Fatty acid (Emersol 871) | 50 | 45.5 | 36.3 |

What I desire to claim and protect by Letters Patent is:

1. A wetness indicating hot-melt adhesive composition comprising:
   (A) 20 to 70 wt.% of total polymer components, said polymer components comprising 35 to 100 wt.% of water sensitive polymer selected from vinyl pyrrolidone homopolymer, vinyl pyrrolidone/vinyl acetate copolymer or a mixture thereof, any balance comprising at least one polymer selected from the group consisting of ethylene/vinyl acetate copolymer, ethylene/acrylic acid copolymer and polyamide,
   (B) 27 to 60 wt.% of organic acid selected from the group of
      (a) at least one free monobasic saturated or unsaturated fatty acid having an acid number above 137, and wherein the proportion of said free monobasic saturated or unsaturated fatty acid to said total polymer components in the composition is such that the pH of the composition, when moist is within a range of 3 to 7;
      (b) 15 to 50 wt.% of the fatty acid in combination with 10 to 55 wt.% of at least one other organic acid having an acid number above 130;
   (C) 0 to 30 wt.% of a water soluble wax;
   (D) a wetness indicating agent capable of causing the composition to change color in response to the presence of moisture in the composition and within said pH range of 3 to 7 in a relatively rapid time compared to that of broadly similar prior art, and in an amount effective to provide the composition with a readily visible color when wet which is distinct from the color of the dry composition.

2. The wetness indicating hot-melt adhesive composition according to claim 1, wherein said other organic acid having an acid number above 130 is selected from the group consisting of rosin, hydrogenated rosin and tall oil acid.

3. The wetness indicating hot-melt adhesive composition according to claim 1, which contains 27 to 60 wt.% of the free monobasic saturated or unsaturated fatty acid.

4. The wetness indicating hot-melt adhesive composition according to claim 1, in which the ratio of said free monobasic saturated or unsaturated fatty acid to said total polymer components is about 1:2 to 2:1.

5. The wetness indicating, hot-melt adhesive composition according to claim 1, in which the wetness indicating agent is Bromophenol Blue.

6. The wetness indicating hot-melt adhesive composition according to claim 1 which contains about 5 to 25 wt.% of water soluble wax.

7. The wetness indicating hot-melt adhesive composition according to claim 1 which contains about 10 to 20 wt.% of water soluble wax.

8. An article comprising a substrate and a coating of the wetness indicating hot-melt adhesive composition according to claim 1 on at least one surface of said substrate.

9. The article according to claim 8, wherein said substrate is a foil substrate.

10. A diaper comprising a moisture absorbent substrate, a water resistant covering for said absorbent substrate, and the wetness indicating hot-melt adhesive according to claim 1 coated on at least a portion of an inner surface of the water resistant covering.

11. A wetness indicating hot-melt adhesive composition comprising:
    (A) 20 to 70 wt.% of total polymer components, said polymer components comprising 35 to 100 wt.% of water sensitive polymer selected from vinyl pyrrolidone homopolymer, vinyl pyrrolidone/vinyl acetate copolymer or a mixture thereof, any balance comprising at least one polymer selected from the group consisting of ethylene/vinyl acetate copolymer, ethylene/acrylic acid copolymer and polyamide,
    (B) 27 to 60 wt.% of organic acid selected from the group of
       (a) at least one free monobasic saturated or unsaturated fatty acid having an acid number above 137, and wherein the proportion of said fatty acid to said total polymer components in the composition is such that the pH of the composition, when moist is within a range of 3 to 7;
       (b) 15 to 50 wt.% of the fatty acid in combination with 10 to 55 wt.% of at least one other organic acid having an acid number above 130;
    (C) 0 to 30 wt.% of a water soluble wax including polyoxyethylene glycol; and
    (D) a wetness indicating agent capable of causing the composition to change color in response to the presence of moisture in the composition and within said pH range of 3 to 7 in a relatively rapid time compared to that of broadly similar prior art, and in an amount effective to provide the composition with a readily visible color when wet which is distinct from the color of the dry composition.

12. A diaper comprising a moisture absorbent substrate, a water resistant covering for said absorbent substrate, and the wetness indicating hot-melt adhesive according to claim 11 coated on at least a portion of an inner surface of the water resistant covering.

13. A wetness indicating hot-melt adhesive composition comprising:
    (A) 20 to 70 wt.% of total polymer components, said polymer components comprising 35 to 100 wt.% of water sensitive polymer selected from vinyl pyrrolidone homopolymer, vinyl pyrrolidone/vinyl acetate copolymer or a mixture thereof, any balance comprising at least one polymer selected from the group consisting of ethylene/vinyl acetate copolymer, ethylene/acrylic acid copolymer and polyamide,
    (B) 27 to 60 wt.% of organic acid selected from the group of
       (a) at least one free monobasic saturated or unsaturated fatty acid having an acid number above 137, and wherein the proportion of said fatty acid to said total polymer components in the composition is such that the pH of the composition, when moist is within a range of 3 to 7;
       (b) 15 to 50 wt.% of the fatty acid in combination with 10 to 55 wt.% of at least one other organic acid having an acid number above 130;

(C) 0 to 30 wt.% of a water soluble wax including polyoxyethylene glycols; and
(D) a wetness indicating agent including Bromophenol Blue capable of causing the composition to change color in response to the presence of moisture in the composition and within said pH range of 3 to 7 in a relatively rapid time compared to that of broadly similar prior art, and in an amount effective to provide the composition with a readily visible color when wet which is distinct from the color of the dry composition.

14. A diaper comprising a moisture absorbent substrate, a water resistant covering for said absorbent substrate, and the wetness indicating hot-melt adhesive according to claim 13 coated on at least a portion of an inner surface of the water resistant covering.

* * * * *

UNITED STATES PATENT AND TRADEMARK OFFICE
CERTIFICATE OF CORRECTION

PATENT NO. : 4,681,576
DATED : July 21, 1987
INVENTOR(S) : Herman Colon and Albert Maletsky It is certified that error appears in the above-identified patent and that said Letters Patent is hereby corrected as shown below:

In the title, Item (54) change "Wetness Indicating Hot-Metal Adhesives" to -- Wetness Indicating Hot-Melt Adhesives --.

Column 1, line 3 and 4, "Wetness Indicating Hot-Metal Adhesives" should read -- Wetness Indicating Hot-Melt Adhesives --.

Signed and Sealed this

First Day of March, 1988

*Attest:*

DONALD J. QUIGG

*Attesting Officer*   *Commissioner of Patents and Trademarks*